(12) United States Patent
DiLemme

(10) Patent No.: US 9,877,815 B1
(45) Date of Patent: Jan. 30, 2018

(54) ELECTRIC FLOSSING DEVICE

(76) Inventor: Anthony V. DiLemme, Seaford, NY (US)

(*) Notice: Subject to any disclaimer, the term of this patent is extended or adjusted under 35 U.S.C. 154(b) by 1297 days.

(21) Appl. No.: 13/238,233

(22) Filed: Sep. 21, 2011

(51) Int. Cl.
*A61C 15/04* (2006.01)

(52) U.S. Cl.
CPC .................................. *A61C 15/047* (2013.01)

(58) Field of Classification Search
CPC ...................................................... A61C 15/047
USPC ........................................ 132/322–327, 329
See application file for complete search history.

(56) References Cited

U.S. PATENT DOCUMENTS

| | | | |
|---|---|---|---|
| 4,458,702 A * | 7/1984 | Grollimund | 132/322 |
| 4,660,584 A * | 4/1987 | Wofford | 132/325 |
| 5,016,660 A * | 5/1991 | Boggs | 132/322 |
| 5,033,150 A | 7/1991 | Gross et al. | |
| 5,217,031 A * | 6/1993 | Santoro | 132/322 |
| 5,279,314 A * | 1/1994 | Poulos et al. | 132/322 |
| 5,301,699 A * | 4/1994 | Craft | 132/325 |
| 5,579,786 A * | 12/1996 | Wolk et al. | 132/322 |
| RE35,712 E | 1/1998 | Murayama | |
| RE36,699 E | 5/2000 | Murayama | |
| 6,526,994 B1 * | 3/2003 | Santoro | 132/322 |
| 7,055,531 B2 | 6/2006 | Rehkemper | |
| 7,311,108 B2 * | 12/2007 | Getgey et al. | 132/322 |
| 7,464,716 B1 * | 12/2008 | Nygren, Jr. | 132/322 |
| 7,793,379 B2 * | 9/2010 | Weiss | 15/167.1 |
| 7,882,845 B2 * | 2/2011 | Filsouf | 132/323 |
| 2002/0178519 A1 | 12/2002 | Zarlengo | |
| 2004/0079384 A1 | 4/2004 | Lai et al. | |
| 2005/0076933 A1 | 4/2005 | Getgey et al. | |

* cited by examiner

*Primary Examiner* — Todd E Manahan
*Assistant Examiner* — Jennifer Gill
(74) *Attorney, Agent, or Firm* — Blank Rome LLP

(57) ABSTRACT

An electric flossing device includes a body, an electromechanical driving mechanism, and a flossing adapter that houses a flossing string insert. The flossing adapter has a head with forward extending arms. String floss is retained at the distal end portions of the arms and moves up-and-down and side-to-side to work the floss down between the user's teeth, while simultaneously scraping the teeth. The flossing adapter and flossing head remains stationary as the flossing string insert moves, to reduce fatigue and avoid injury to the user. This motion emulates manual flossing and permits the device to be moved forward and back slightly to follow the entire curvature of the tooth and ensure complete cleaning.

14 Claims, 14 Drawing Sheets

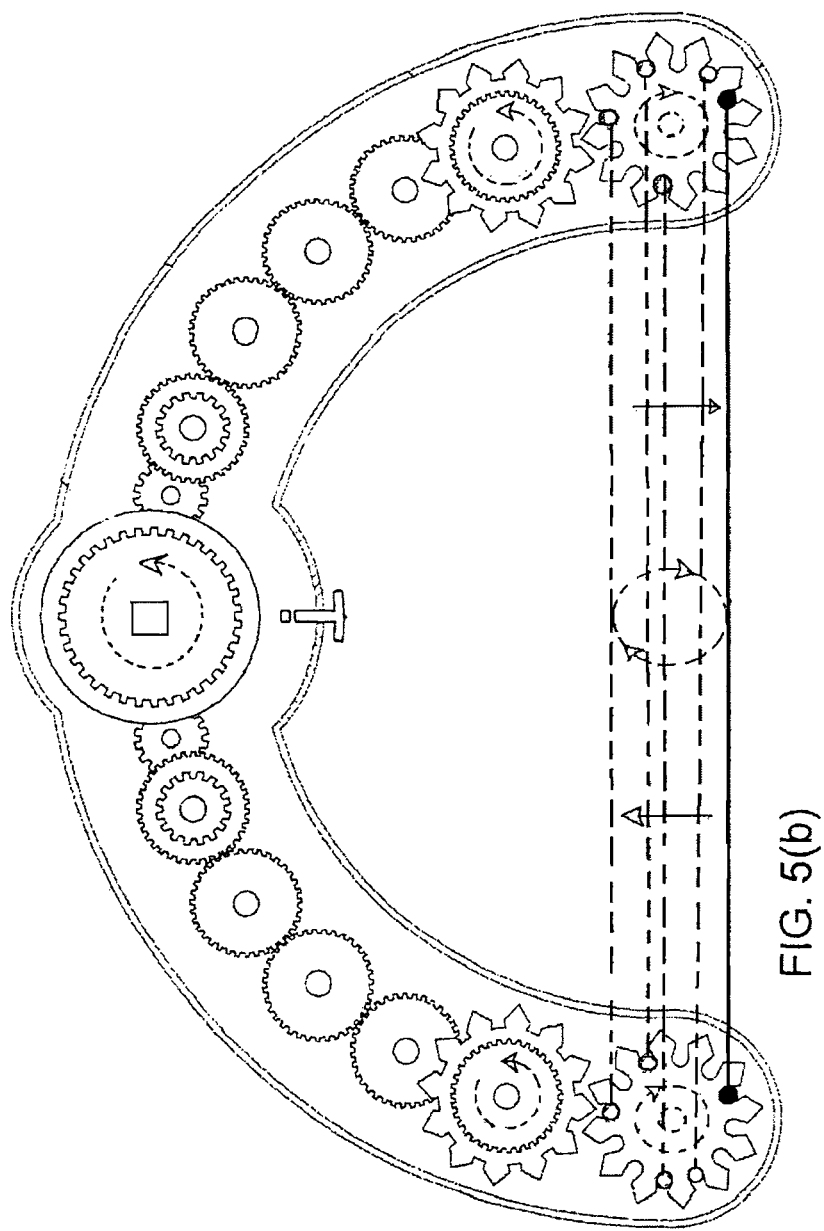

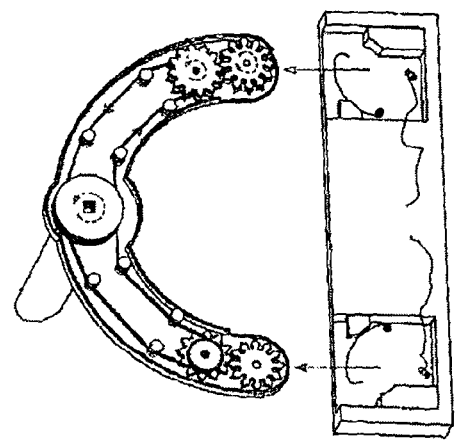
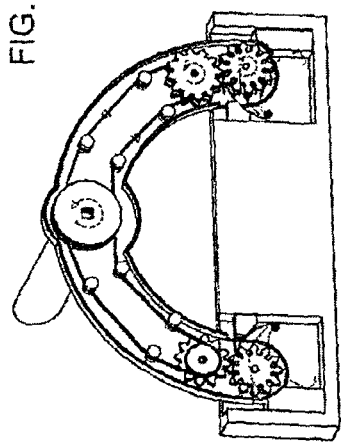
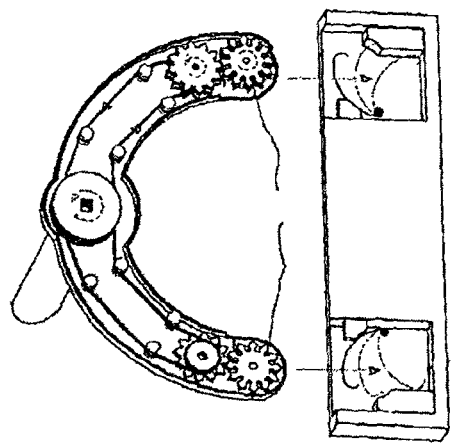
FIG. 8

ELECTRIC FLOSSING DEVICE

BACKGROUND OF THE INVENTION

Field of the Invention

The present invention relates to a motorized flossing device. More particularly, the present invention is an electric flossing device having an ergonomic handle body, an electro-mechanical driving mechanism, a removable flossing adapter, a disposable flossing string insert and a flossing string insertion/removal mechanism. When powered, this flossing device best emulates the motion and maneuverability of traditional manual string flossing.

Background of the Related Art

Traditional flossing is done by wrapping floss, which can be for instance string or nylon, around a person's fingers and inserting the floss into the user's mouth. The floss is then worked in a side to side/up and down motion between the teeth to scrape the sides of the teeth and stimulate the gums. This process is quite effective, however flossing can be difficult, painful, timely and frustrating for some people, particularly children, teenagers, seniors, or anyone that is challenged with the grief of flossing. This process can cause discomfort to the user's hands and fingers especially when reaching for hard to reach areas like the molars.

Automated flossing devices have been developed to assist people with the tedious task of flossing. Motorized flossing devices already exist, for instance, by U.S. Pat. No. 7,055,531 to Rehkemper; U.S. Pat. No. 7,311,108 to Getgey; however they do not maintain the constant taut string tension that is necessary to effectively clean the sides of teeth and stimulate the gums. Their flossing string weakens after a few uses and becomes flimsy and ineffective. They are not easy to use and do not emulate the oscillating motion similar to traditional flossing. They utilize obvious erratic mechanical movements not easily controlled by the user. These mechanical movements are not contained and are dangerous due to the unprotected moving parts in the mouth. If not used properly these moving parts are inevitably a high risk and can damage the teeth and gums. In addition, those devices utilize large and expensive attachments which are not practical for disposal and everyday use.

SUMMARY OF THE INVENTION

Accordingly, it is an object of the invention to provide a safe user friendly motorized flossing device which is easy to use and eliminates the frustration and fatigue associated with traditional manual flossing. It is a further object of the invention to provide an electronic flossing device that emulates the oscillating motion of traditional manual flossing. It is another objective to provide a flossing head which has a constant taut flossing string insert at all times providing floss tension control to effectively clean the sides of teeth above and below the gum line. It is an objective to have no exposed moving parts in the user's mouth except for the flossing string itself. It is a further objective to provide inexpensive and removable/replaceable flossing adapters. It is still a further object of the invention to provide inexpensive disposable flossing string inserts that are practical to be purchased and disposed for a single daily use.

An electric flossing device includes a body, an electro-mechanical driving mechanism, and a flossing adapter which houses a flossing string insert. As shown, the body has a round or slender base, neck, and head. These bases are ergonomically designed to fit in the palm of a user. The electromechanical driving mechanism includes a gear box and a shaft which extends the length of the neck and protrudes out of the distal end of the neck. The flossing adapter is removably engaged with the distal end of the shaft, and can be easily removed, discarded, and replaced. The shaft rotates the flossing adapter's main gear which drives a flossing string insert to move in a back and forth oscillating manner. The flossing adapter is designed to create both an up-and-down and side-to-side rocking motion to work the floss down between the user's teeth, while simultaneously scraping the teeth. This motion emulates manual flossing and permits the device to be moved forward and back slightly to follow the entire curvature of the tooth and ensure complete cleaning.

These and other objects of the invention, as well as many of the intended advantages thereof, will become more readily apparent when reference is made to the following description, taken in conjunction with the accompanying drawings.

BRIEF DESCRIPTION OF THE FIGURES

FIG. 5(b) is a top view of the flossing head showing movement of the flossing string;

FIG. 8 shows removal of the flossing string inserts from the flossing head;

DETAILED DESCRIPTION OF THE PREFERRED EMBODIMENTS

Figure 1:
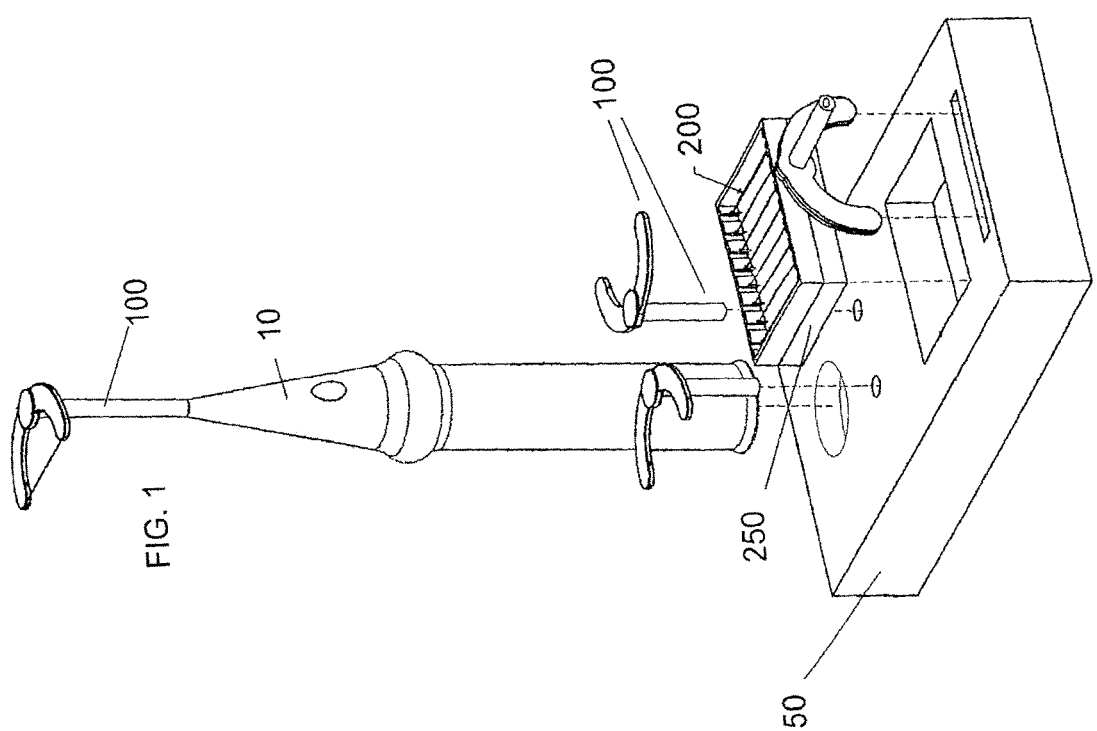
FIG. 1 is a perspective view of the flossing device storage base with the flossing device.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

Figure 2:
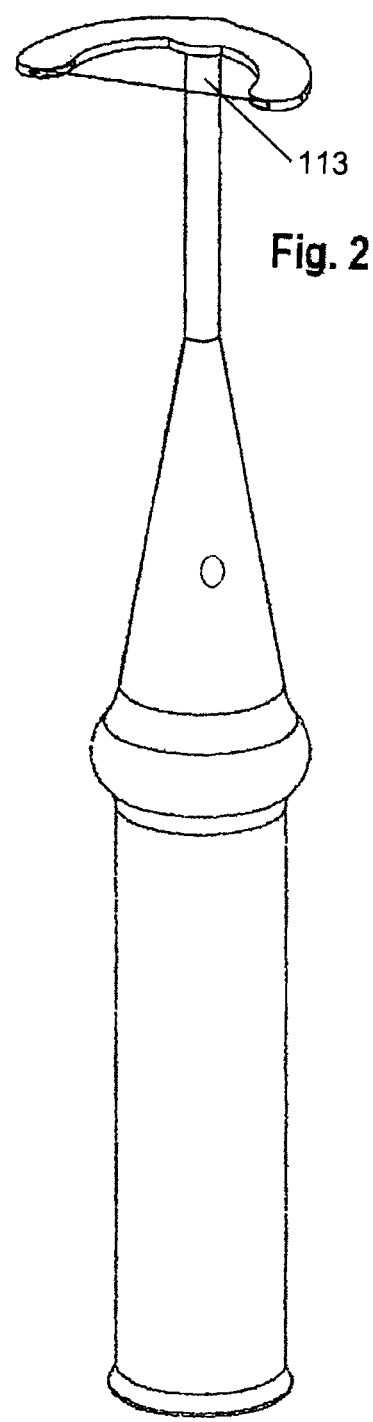
FIG. 2 is a perspective view of the motorized flossing device.
Figure 3:
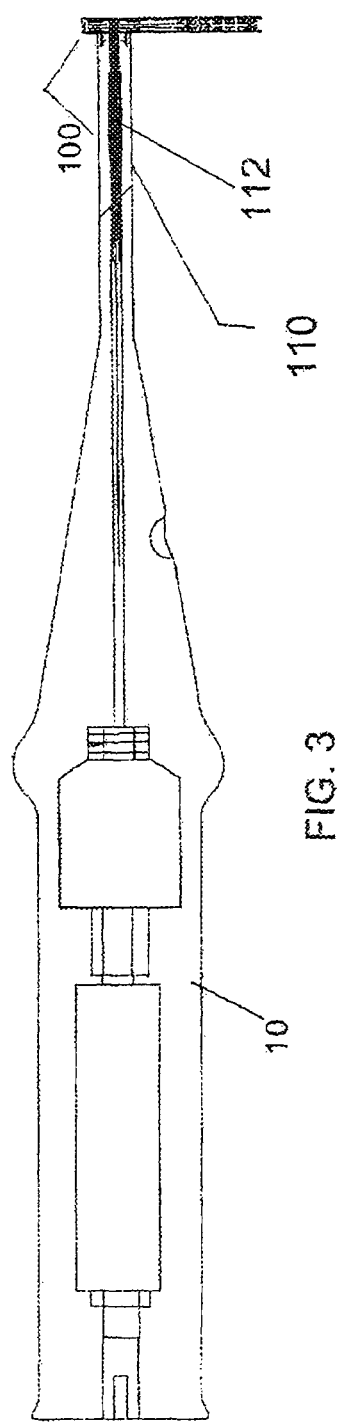
FIG. 3 is a cutaway view of the flossing device showing the inner components.

Turning to the drawing, FIG. 1 shows the motorized flossing device 5 in accordance with a preferred embodiment of the invention. The electric automated flossing device 5 includes a durable plastic elongated main body 10, a base/charger 50, a removable/replaceable flossing adapter 100, disposable flossing string inserts 200, and a flossing string insertion and removal tray 250. The flossing adapters 100 can be stored in circular openings in the storage base which hold the stem or extended slots which retain the flossing head. As shown in FIGS. 2-3, a light 113 is provided to illuminate the inside of the user's mouth to facilitate placement of the floss between the user's teeth. The light 113 is located on the stem of the flossing adapter just below the flossing head, and is directed outward from the stem and upward (in the embodiment) toward the floss.

Turning to FIG. 3, the main body 10 is preferably a single elongated one-piece unitary and integral member. It has a base with a flat end so that the body 10 can stand on the flat end. The base connects to a wide end of a tapered handle. An opposite narrow end of the handle connects with a main stem. The entire body 10 preferably has a hollow interior and access can be provided to the interior to insert, remove and/or replace the components stored within. The main stem has a central bore, and the distal end is set at an angle.

As further shown in FIG. 3, an electro-mechanical driving mechanism is housed within the main body 10. The electro-mechanical driving mechanism provides the power and driving force needed to drive the flossing adapter to create the flossing action. The electro-mechanical driving mechanism includes a motor, a gear box, a disposable or rechargeable battery, a battery compartment, an on/off button and a central drive shaft. The battery provides power to the motor, which operates via the gear box to rotate the drive shaft at a preset (or user-selectable) speed. The on/off button turns the motor on and off. A speed selection switch can also be provided to permit the user to select the speed or force with which the motor operates. The drive shaft extends from the gear box to a distal end portion of the main stem through the main stem central bore.

Figure 4:
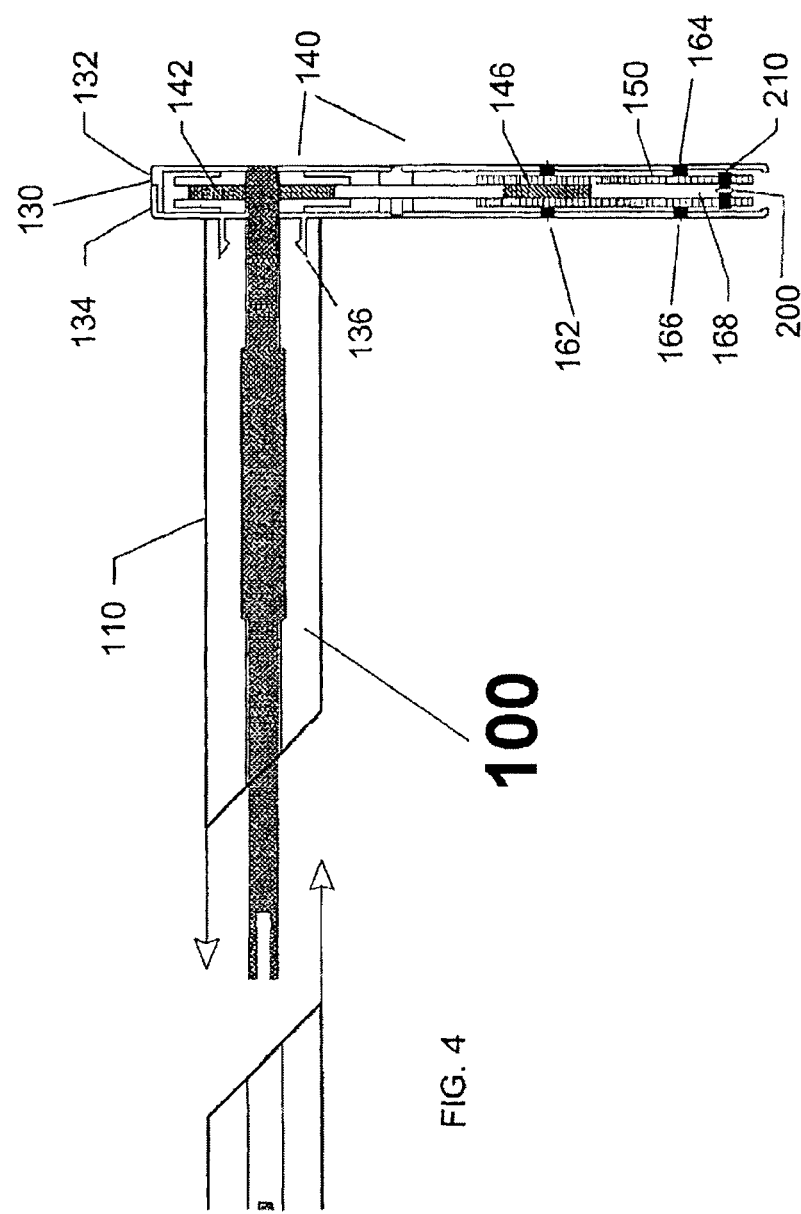
FIG. 4 is a side cutaway view of the flossing adapter showing the stem and flossing head.

Turning to FIG. 4, the flossing adapter 100 is shown having an adapter stem 110 and a flossing head 130. The removable flossing adapter 100 is a one piece mechanism where a flossing head is adjoined to a flossing adapter stem at a 90 degree angle, which gives the user the best visibility and maneuverability. It will be apparent, however, that any suitable angle can be provided. In addition, the distal end of the flossing adapter stem 110 is set at an angle which is configured to align with the distal end of the main stem. The angled ends are arranged so that the flossing head 130 is aligned in a desired manner so that it is easy to position in the user's mouth. The flossing adapter stem 110 defines a central bore in which a flossing adapter drive shaft 112 is located.

The flossing adapter 100 is removeably attached to the main body 10. The flossing adapter stem 110 and the main stem are configured so that the flossing adapter stem can be readily and reliably attached and detached from the main stem. The stems can further be configured so that one stem slides into the other stem with a friction fit to provide a more reliable connection when attached. Alternatively, the stems can each have respective mating fastening mechanisms, such as threading, tongue and groove, snap fit, or the like.

Likewise, the main drive shaft and the flossing adapter drive shaft 112 are configured to be readily and reliably attached and detached to each other. For instance, the mating end of the main drive shaft and the mating end of the flossing adapter drive shaft 112 can each have mating arms or the like. The drive shaft 112 can also have a wide section to further strengthen the shaft. The main drive shaft and the mating end shaft are automatically aligned with one another when the distal end of the main body is aligned with the distal end of the flossing adapter stem 110. The main drive shaft is also guided by the sides of the central bore. Accordingly, the flossing adapter 100 can be removed from the main stem and stored on the cradle base (FIG. 1) to be changed with another flossing adapter or replaced with a new one.

As further shown in FIG. 4, the flossing head 130 can be comprised of a top case 132 and a bottom case 134. A circular adapter foot 136 projects outward from the bottom surface of the bottom case 134. The adapter foot 136 slides into the central bore of the flossing adapter stem 110 about the flossing adapter drive shaft 112. The central bore can be wider toward the distal end of the adapter stem to receive the adapter foot 136. Or, the adapter foot 136 can be received in a circular groove which is positioned in the end of the adapter stem 110 outside of the central bore.

Figure 5A:
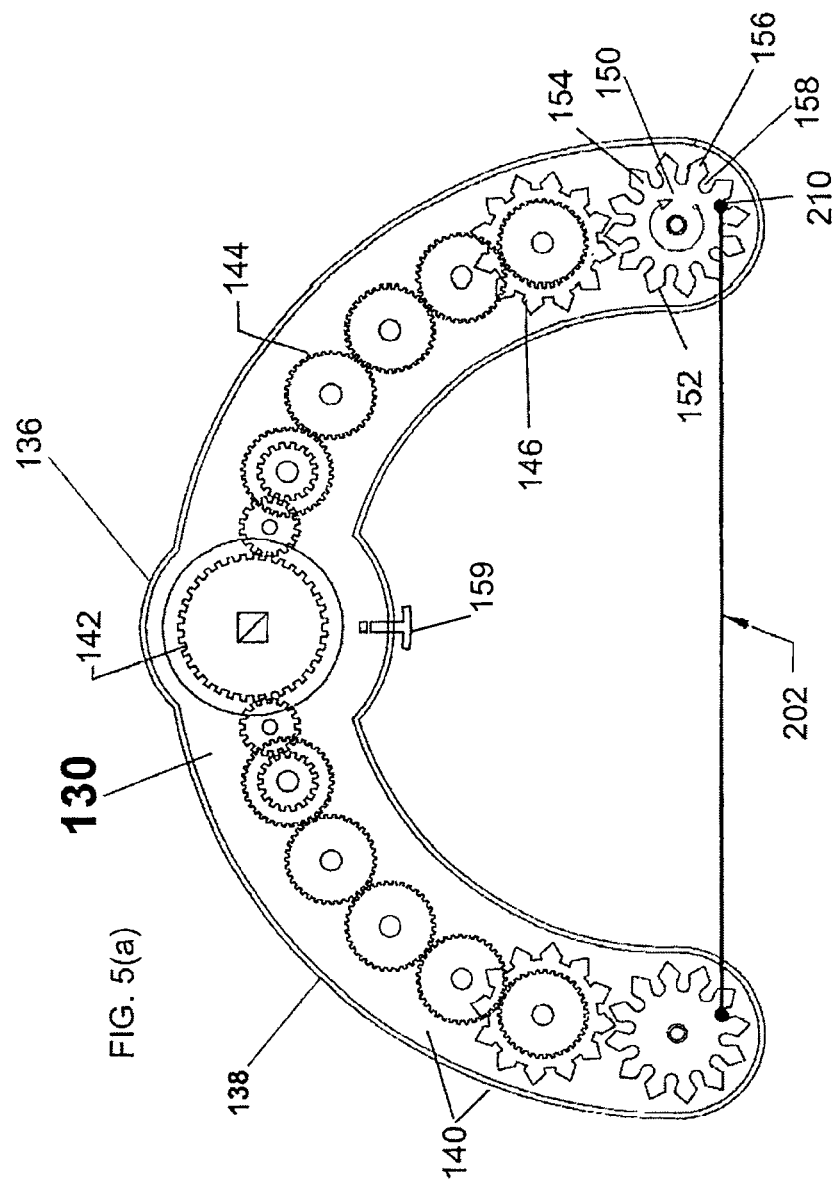
FIG. 5(a) is a top view of the flossing head showing gears in accordance with one embodiment of the invention.

Referring now to FIG. 5(a), the flossing head 130 is shown in greater detail. The flossing head 130 is generally configured to be semi-circular and symmetrical about the center. Thus, the flossing head 130 generally defines one-piece unitary body having a central hub 136 with curved arms 138 extended outwardly there from. The distal ends of the arms 138 are also curved, and define a flossing distance. The flossing distance is wider than a user's widest tooth, but is not too large so that the head 130 has trouble reaching hard to reach places in the user's mouth. Different size heads 130 can be provided with a smaller flossing distance for use by children or small animals (such as dogs), and larger sizes can be provided for use by adults or larger animals. The entire flossing head 130 is configured to be ergonomic and without any sharp features or protruding members which could otherwise injure the inside of the user's mouth. The flossing head 130 is also thin (as best shown in FIG. 4) so that it can be manipulated in hard to reach places within the user's mouth.

As shown in FIG. 4, the top case 132 slides or snaps into the bottom case 134. It will be apparent however that the head 130 can be a single unitary device and not two separate pieces. An access or opening is provided in the cases 132, 134 at the distal ends of the arms 138 to permit the flossing string to move between the arms 138 and for the insertion/removal of the flossing string insert 200. All moving elements in the flossing head 130 are entirely enclosed within the top and bottom plastic casing 132, 134 to preserve the parts and to protect the safety of the user's mouth from being exposed and damaged by the moving parts.

Returning to FIG. 5(a), the cases 132, 134 of the flossing head 130 house a drive mechanism 140 comprised of a number of gears. The main gear 142 is located at the central hub 136 of the head 130. The main gear 142 is coupled with (directly or indirectly) the flossing adapter drive shaft 112. For instance, the main gear 142 can have a square-shaped center opening which receives the head of the flossing drive shaft 112. The main gear 142, in turn, is coupled via one or more intermediary drive gears 144 to a translation gear 146. The translation gear has a first set of external teeth which couple with the teeth of the last intermediary drive gear 144, and a second set of external teeth which couple with a working gear 150. The first set of teeth can be straight teeth, though any suitable configuration can be provided. The drive gears 144 are located within the arms 138 of the flossing head 130, and the translational gear 146 and working gear 150 are located at the distal end portions of the arms 138.

The working gears 150 are each configured to receive a flossing pin 210. The working gears 150 have a plurality of external cogs or teeth 152. The teeth 152 have a narrow base 154 which taper outward to a head 156 which is tapered inwardly sharply to form a triangular shape. This configuration defines a channel 158 between the teeth 152. The channel 158 has a wide bottom and is slightly narrowed at the entry point or gate. Accordingly, the pins 210 can be snapped into the channels 158. However, the narrowed gate will retain the pins 210 in the channels 158 without coming free during use. The main gear 142 is held in position by the drive shaft 112. The drive gears 144 each receive a retention pin through a center opening which is held in position by the top and bottom cases 132, 134.

Referring to FIG. 5(b), operation of the flossing head 130 is shown. The flossing pins 210 are received in the channels 158 of the working gear 150. Flossing string 202 is coupled with the pins 210, so that the flossing string 202 spans across the flossing distance created between the distal end portions of the arms 138. As the drive shaft 112 rotates, the working gears 150 rotate. The direction of the gear rotations is shown by the arrows. The working gears 150 both rotate in the same direction (clockwise in the embodiment shown) and at the same speed. Accordingly, the distance between the pins 210 remains the same as the pins 210 translate within the channels of the working gears 150. In addition, the pins 210 move in a first direction, i.e., in and out (up and down in the embodiment of FIG. 5(b)) with respect to the front face of the flossing head 130. The pins 210 also move in a second direction, i.e., transverse or side to side direction (left and right in the embodiment shown) with respect to the arms 138. The motion of the flossing string 202 is reflected by the arrows. The distance of the motion in each of the first and second directions is based on the diameter of the working gear 150. Accordingly, those distances can be adjusted by providing working gears 150 of different sizes. In addition, it should be noted that while the invention provides motion in a first and second direction, a configuration can be provided which has motion in only one of those directions, and/or in a different direction.

Hence, the arms 138 remain stationary as the flossing string 202 emulates manual flossing by oscillating in and out and side to side. When positioned between a user's teeth, the device can be held stationary and the flossing string 202 will move upward and downward, and side to side, between the teeth. The user can also move the device so that the flossing string 202 moves toward and away from the teeth when positioned in the gap between the teeth.

Figure 6A:
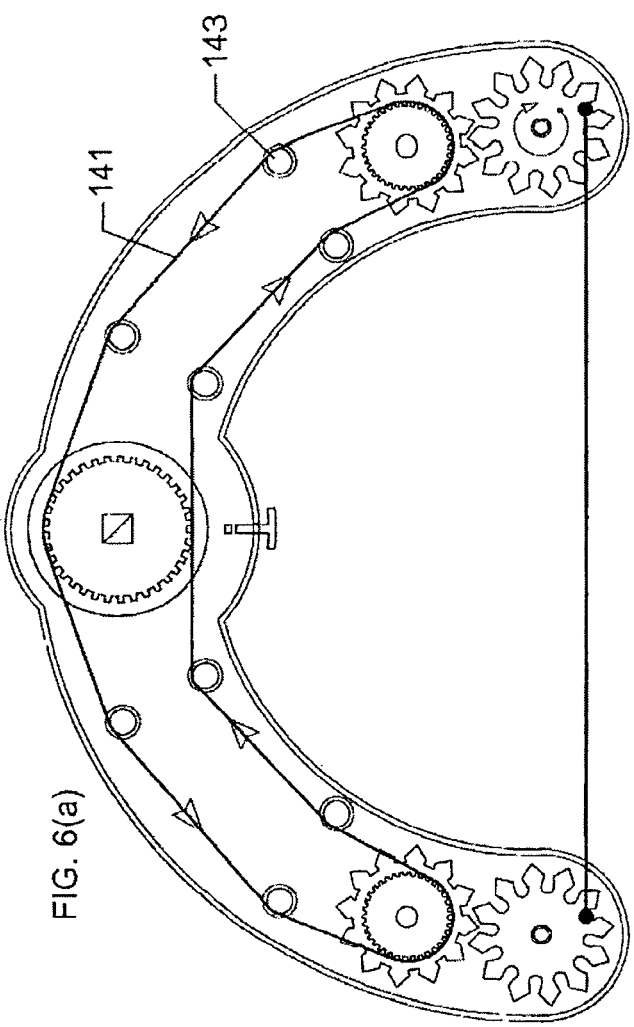
FIG. 6(a) is a top view of the flossing head showing a drive belt in accordance with an alternative embodiment of the invention.

Turning to FIG. 6(a) and alternative configuration for the drive mechanism 140 is shown. Here, the drive gears 144 of FIG. 5(a) have been removed and replaced by a drive belt 141 and various belt rollers 143 (with or without teeth) positioned along the arms 138. The rollers 143 can have a wide ends and a thinner middle which engages the drive belt 141. The drive belt 141 is driven by the main gear 142 by respective teeth, which in turn drives the translational gears 146.

Figure 6B:
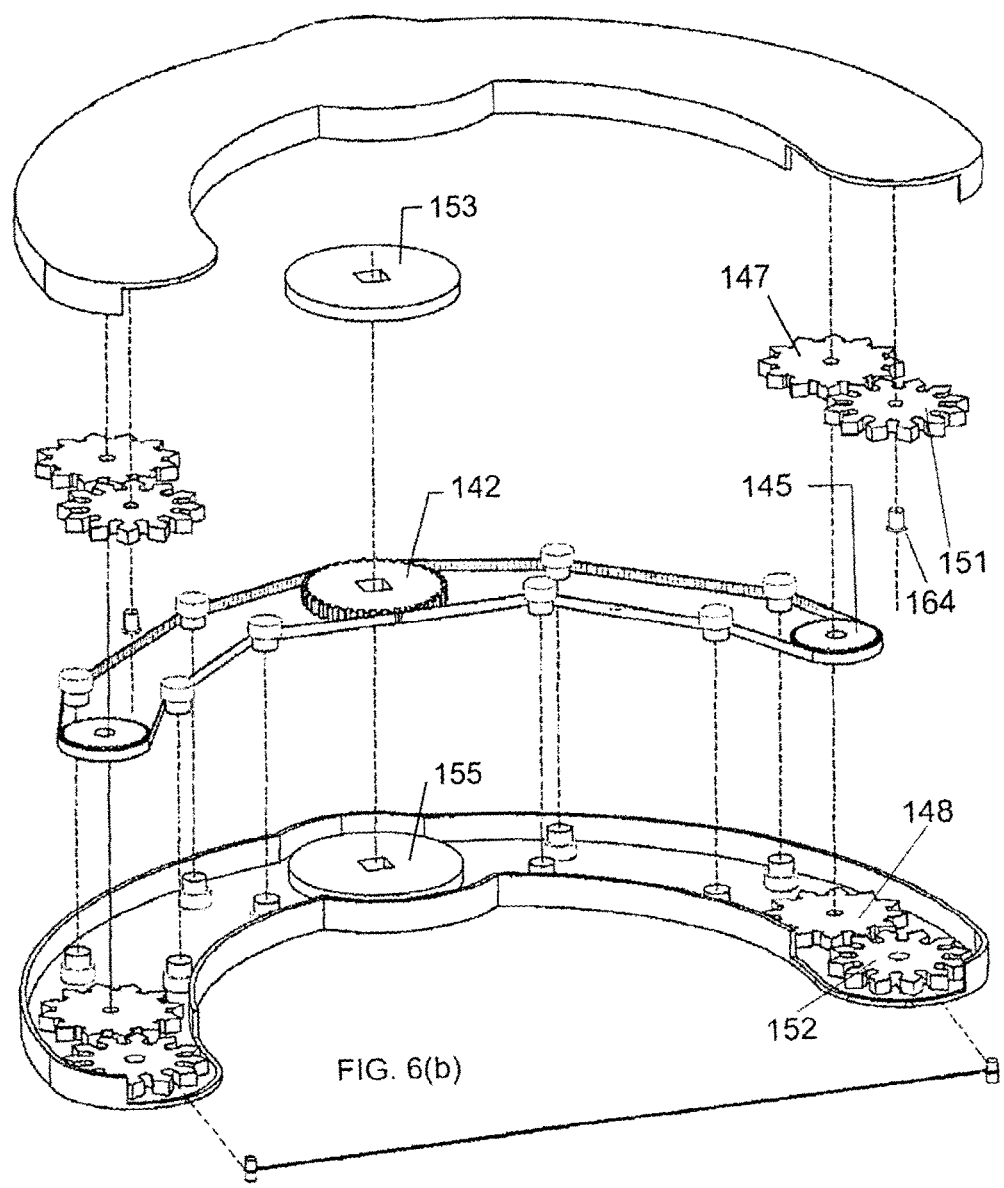
FIG. 6(b) is an exploded view of the flossing head of FIG. 6(a)

The translational gears 146 and working gears 150 have the same construction in each of the embodiments where the translational gears 146 connect with the drive gears 144 (FIG. 5(a)) and where the translational gears 146 connect with a drive belt 141 (FIG. 6(a)). The construction and operation of the translational gears 146 and the working gears 150 is best shown in FIGS. 4 and 6(b). As shown, the translational gears 146 have two external or outer plates, namely a top gear plate 147 and a bottom gear plate 148. And, an internal plate 145 sandwiched between the two external plates 147, 148. The internal plate 145 is connected to the external plates 147, 148 so that all the plates rotate together. The internal plate 145 engages with the drive gears 144 or the drive belt 141 and translates that power to the external gears 147, 148. The top and bottom plates prevent the drive gears 144 or drive belt 141 from disengaging the internal plate 145, and also align with the two plates of the working gears 150. A single retention pin 162 can extend through the center of each of the external and internal plates 145, 147, 148 to keep the gears in the proper position and alignment.

The working gears 150 also each comprise a top gear plate 151 and a bottom gear plate 152. The top working plate 151 is secured to the top casing 132 by a first retention pin 164. The bottom working plate 152 is secured to the bottom casing 134 by a second retention pin 166. The retention pins 164, 166 have a head which prevents the respective working plate 151, 152 from slipping off of the pin 164, 166. Accordingly, the working plates 151, 152 are held separate and apart from each other so that there is a space 168 between the working plates 151, 152 (as best shown in FIG. 4). The flossing string 202 enters this space 168 during operation of the device. This keeps the middle of these two gears totally clear to allow the flossing string 202 and insert/pin 210 to rotate 360 degrees with no obstructions in its way.

In addition, the retention pins 164, 166 maintain the working plates 151, 152 in alignment with the top/bottom plates 147, 148 of the translational gears 146. So, the translational plates 147, 148 can drive the working plates 151, 152 in a synchronized manner. Thus, the working plates 151, 152 rotate at the same time and speed as each other even though they are not connected to one another.

Figure 6C:
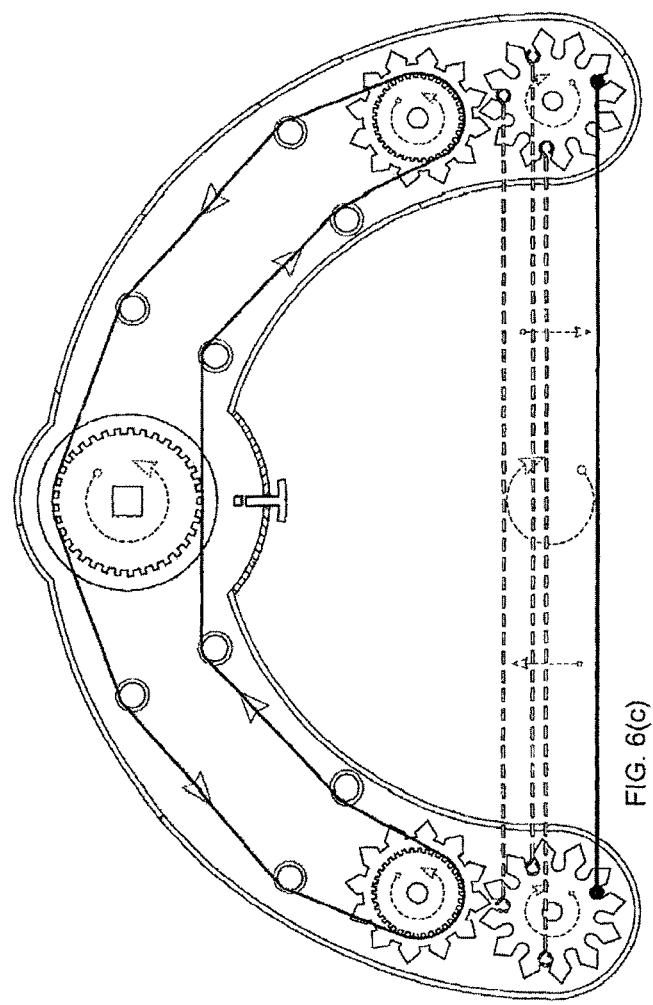
FIG. 6(c) is a top view of the flossing head of FIG. 6(b) showing movement of the flossing string.
Figure 6D:
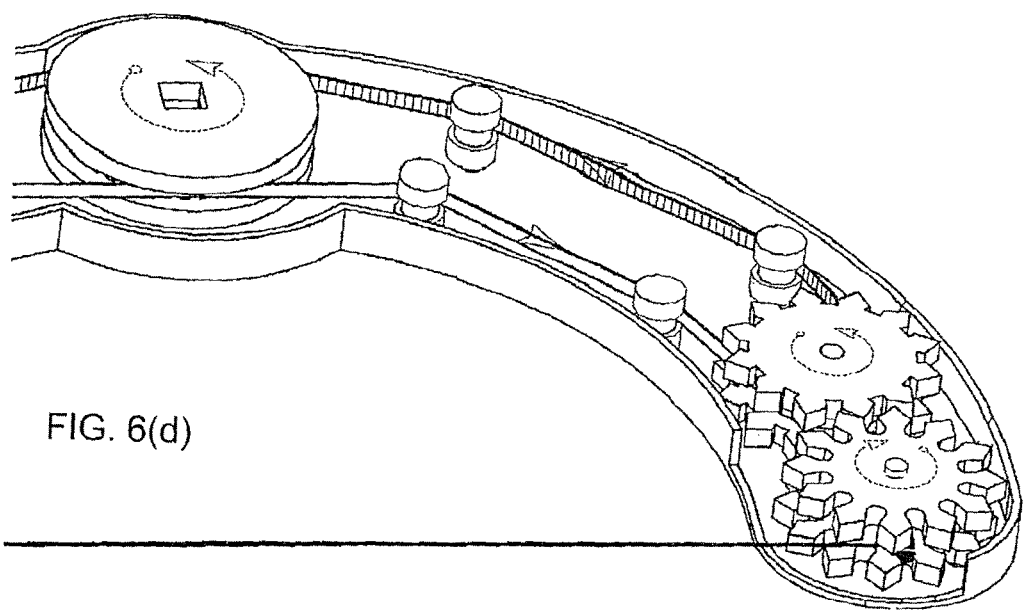
FIG. 6(d) is a perspective view of the flossing head showing connection to the flossing pin and floss string.

As shown in FIGS. 6(b)-(d), the opening in the casing (for the embodiments of FIGS. 5(a) and 6(a)) extends along a portion of the front and inner side of the casing to permit the desired motion of the flossing string 202. In addition, outer guide plates 153, 155 are positioned above and below the main gear 142 to guide the drive belt and ensure that the guide belt does not disengage from the main gear 142. For both FIGS. 5 and 6, the main gear 142 is the primary rotating gear that drives all of the other connecting gears. This eliminates any need for additional powered driving mechanisms in the flossing head 130. The all/gear (FIG. 5) and the gear/belt (FIG. 6) have one main gear 142 which activates the next connecting gears, to then activate the final working gears 150.

Figure 7C:
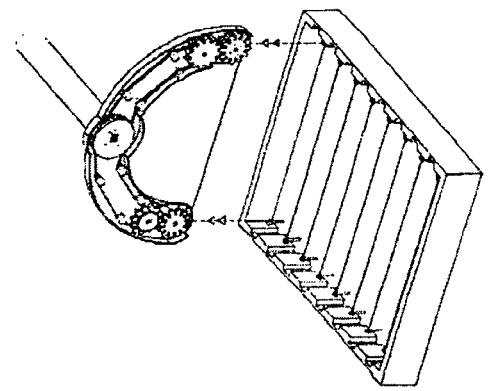
FIGS. 7(a)-(c) show insertion of the flossing string inserts to the flossing head, with the top cover of the flossing head removed to better illustrate the connection between the string inserts and the gears of the flossing head.
Figure 7B:
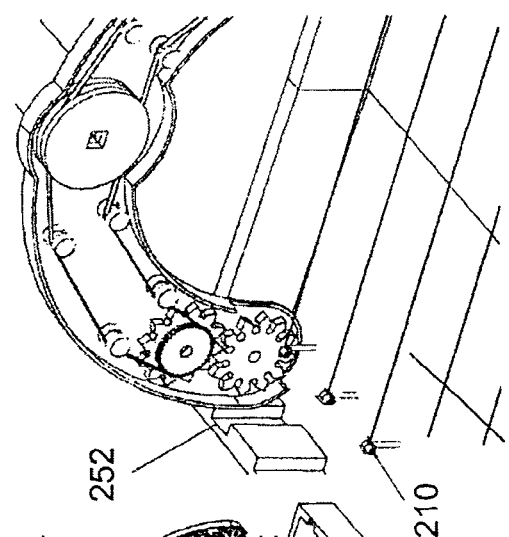
Figure 7A:
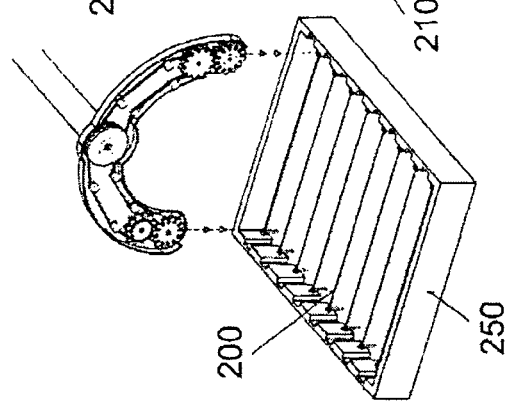

Turning to FIGS. 7(a)-(c), detail of the flossing string inserts 200 and the two-sided pre-set multiple flossing string insert tray 250 is shown. The flossing string inserts 200 are formed by two flossing pins 210 and a flossing string 202. The flossing pins 210 are small cylinders, or alike, which are orthogonally connected with the flossing string 202. A central groove (best shown in FIG. 4 and FIG. 6b) is formed circumferentially about the center of the flossing pins 210. The groove receives the flossing string 202 to prevent the string from sliding along the length of the flossing pins 210. The flossing string 202 is affixed within the groove, such as by tying or attaching the flossing string 202 to the pin 210 or by other suitable means. The flossing string 202 can be one integral piece having two looped ends which receive the flossing pins 210. This allows the string 202 to move freely around the pin 210 without winding/kinking during the oscillating operation. The flossing pins 210 are located at the two opposite ends of the flossing string 202. The length of the flossing string insert 200 is slightly smaller then the flossing distance between the two arms 138 of the flossing head 130. In this manner, the flossing string 202 will remain taut between the flossing pins 210 when the flossing insert 200 is positioned in the flossing head 130. The flossing string 202 can be a nylon (or similar) string.

The flossing string insert 200 is pre-fitted together with flossing pins 210 and set into a flossing insert tray 250. The tray 250 has a bottom, front wall, rear wall, and two side walls. A plurality of sets of grooved guide slots 252 are positioned along the side walls. The flossing pins 210 are positioned to be aligned with the guide slots 252 with the string 202 extending there between. The flossing pins 210 together with the flossing string insert 200 can be pre-mounted to posts or the like as a temporary position holder.

The process for fitting the flossing string insert 200 to the flossing head 130 is shown in FIG. 7(a). It should be noted that the top cover of the flossing head 130 is removed to illustrate the connection between the flossing string inserts 200 and the gear 152 of the flossing head 130. In operation, the top cover stays attached to the flossing head 130 when the flossing string insert 200 is attached and removed from the flossing head 130, so that the flossing head 130 remains a closed unit.

The guide slots 252 receive the flossing head 130 and align the flossing head 130 with the flossing pins 210. The head 130 is aligned with the tray 250 at a 90 degree angle to the grooved slots. At FIG. 7(b), the user pushes the flossing head 130 downward in the tray 250 until the flossing pins 210 snap into the tightly fitted channels 158 of the working gears 150. The head 156 of the teeth 152 of the working gears 150 are angled to further guide the flossing pins 210 into a guaranteed position of the channels 158. At FIG. 7(c), the user then removes the flossing head 130 from the tray 250 with the flossing string insert 200 and flossing pins 210 attached to the working gears 150.

When the flossing pins 210 on the flossing string insert 200 are fully snapped into place on the working gears 150, the flossing pins 210 are stretched outward slightly to maintain continuous tension on the flossing string 202. The string tension remains constant at all times until the flossing string 202 is broken and/or replaced. This ensures a consistent reliable taut flossing string 202 insert during operation, which guarantees a proper and effective cleaning. The tray 250 is a plastic disposable tray which can be disposed of when all of the flossing string inserts 200 have been used.

The flossing string removal is also a fast and easy process. When the flossing string 202 breaks or flossing is terminated, it is ready to be replaced. This can be done by using the flossing string removal mechanism, FIG. 8. The removal mechanism is an upright member which has two compartments with a flossing head stop, a spring lever, and a spring lever stop. The spring lever has one end which is fixed to the wall of the removal mechanism, and an opposite end formed as a hook. The flossing string insert 200 is removed from the flossing adapter by aligning the head of the flossing adapter 130 at a 90 degree angle to the two grooved slots on the cradle base. This removal mechanism can be incorporated in the flossing device storage base 50 shown in FIG. 1. The flossing device storage base includes a flossing device handle storage, flossing adapter storage, flossing string insert tray storage, and flossing string insert removable mechanism.

The flossing head adapter 130 is then pressed gently all the way down into the base. The two spring hooks on each side are now sprung in the horizontal position ready to hold back the flossing pins 210 and flossing string insert. The hooks enter the space 168 between the working gear plates 151, 152 and grab the flossing pins 210. The flossing head is now ready to be lifted straight up. At this time the flossing adapter 130 is stripped of the old flossing string insert 200 and is ready to be stored or a new string insert can be re-applied. The used flossing string inserts 200 fall into the base unit. The used/broken string inserts can be discarded from the base at anytime.

The flossing adapter is designed to activate a flossing string insert 200 to create an oscillating side-to-side/up and down parallel motion maintaining a continuous taut flossing string 202 at all times. This allows the flossing string to be maneuvered down between the user's teeth, simultaneously scraping the sides of the teeth. The oscillating motion activates the flossing string insert rapidly to easily slide between the teeth. This is especially helpful for tight teeth and back teeth. These described motions can remove plaque and bacteria particles trapped between teeth and stimulate gums, which can help reduce gingivitis, tooth decay and serious gum disease.

While the user grasps the handle of the flossing device and turns the power on, the oscillating side-to-side and up and down flossing string motion of the flossing head is in effect. The user now has the ability to guide the flossing string in between their teeth lifting the device gently up and down while pushing and pulling forward and back to guide the flossing string to follow the entire curvature of the teeth above and below the gum line. It is important that the flossing string insert remains taut during operation to obtain floss tension control in order for this motion to work properly. This described flossing device does so by emulating the movements of traditional manual flossing. During this procedure, for safety of the user, there are no moving parts in the user's mouth except for the flossing string insert itself.

Figure 9:
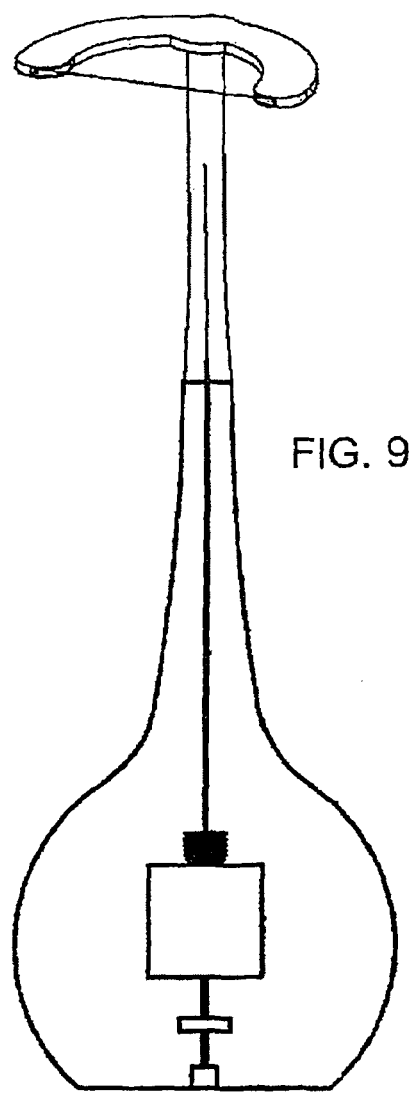
FIG. 9 shows a ball-grip handle for use with the invention.

The flossing adapter stem 110 is removable and replaceable from its stem which is connected to a straight or such ergonomic handle. An optional handle can consist of a tapered narrow stem connected to a rounded-ball grip body (FIG. 9) that is ergonomically designed to fit in the palm of a user's hand, which can help maneuverability at all angles. These and other suitable motorized handles and styles can be utilized to adapt/connect to the flossing adapter to utilize the benefits of the flossing adapter technology.

The flossing adapter is replaceable or interchangeable for multiple users. The flossing adapter may also have a small light affixed to the flossing adapter stem or flossing head to turn on with the operation of the main flosser to help visibility in the user's mouth. The specially designed flossing adapter makes it safe to use and easy to clean those hard to reach areas where a toothbrush can't reach.

The flossing head utilizes an inexpensive flossing string insert that is disposable after a few uses or according to the user's discretion. The flossing head houses a series of small plastic gears OR a gear/belt combo. The small gears and drive belt can be made out of similar cost effective materials.

When powered and ready for use, the subtle movements aid the flossing string insert to find the path of least resistance when pressed down between the teeth which allows easier penetration under the gum line, and less force is needed while pushing into the gap between the teeth. In normal traditional flossing, pressure may be applied until the floss pops through the teeth, especially teeth with tight contacts, and the momentum can carry on and painfully impact the gum tissue. This can be reduced or avoided with this motorized flossing device especially allowing the user to have more control at all angles.

This described automated device eliminates the hard work of flossing by replicating the action of manual flossing. This flossing device could encourage the average flosser and inspire non flossers. This flossing device can be used by dentists and hygienists alike.

For a safety option, a vertical power/kill pin button (FIG. 5(*a*)) is set on the top portion of the flossing adapter head 130 at the central hub 136 between the two arms 138. This pin is a safety shut off that limits the user to not push down too far as to lacerate and endanger the gum tissue. The safety button would be pressed in if it makes contact with the flat surface of the teeth or calibrated similarly, indicating that the user has inserted the device too far down between the teeth. In response, the power to the unit would shut off and the flossing string movement is stopped as to limit the depth of penetration to the gum line and reduce the possibility of the user being cut. Pressing the on button turns the unit on again.

Another option is to provide vibration to the flossing adapter to help sooth and massage the gums. The movement would also help in temporarily separating tooth and gum for the flossing string to get through creating an easy passage of floss between tight adjoining teeth. Less pressure would be needed and the user could have more control and assertiveness with using the motorized device in their mouth.

Figure 10:
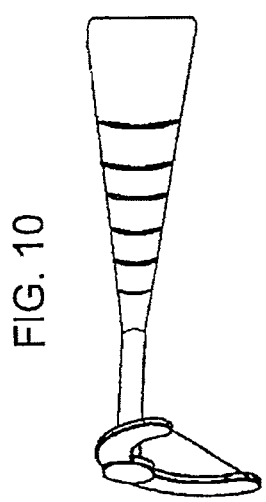
FIG. 10 shows a miniature flossing device in accordance with the invention.

Other options of the invention include that the battery types can be built-in the handle. The batteries can be rechargeable with the cradle base charger or disposable alkaline. The flossing adapter, flossing head, flossing string insert and handle can be made smaller for kids and travel sizes. The entire flossing adapter concept can be offered with a miniature handle, as shown in FIG. 10. The flossing string inserts can be offered in different flavors, i.e. grape, cherry. And, a light can be added at the top of the flossing adapter for better visibility.

The foregoing description and drawings should be considered as illustrative only of the principles of the invention. The invention may be configured in a variety of shapes, colors and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

I claim:

1. A flossing device for use with floss, said device comprising:
   an elongated body having a longitudinal axis;
   a flossing head having a first stationary arm and a second stationary arm, the first and second arms extending perpendicularly outward from said body and creating a space between distal end portions of the first and second arms;
   a floss retention device configured to receive floss at the distal end portions of the two arms so that the floss extends across the space transverse to the longitudinal axis of said body, wherein said floss retention device includes a first working gear housed at the distal end portion of the first arm and a second working gear housed at the distal end portion of the second arm, whereby the first and second working gears each have teeth with a channel therebetween; and,
   a driving mechanism housed within said flossing device and configured to drive the floss retention device to move the floss.

2. The flossing device of claim 1, wherein said flossing head remains stationary with respect to said flossing device as the driving mechanism is operated.

3. The flossing device of claim 1, the floss having a first end and a second end opposite the first end, and further comprising a first flossing pin and a second flossing pin configured to retain the floss therebetween, the first end of the floss fixedly attached to the first flossing pin and the second end of the floss fixedly attached to the second flossing pin, said first flossing pin fixedly received in the channel of said first working gear and said second flossing pin fixedly received in the channel of said second working gear.

4. The flossing device of claim 1, wherein said working gear includes a top gear plate rotatably affixed to a top of said flossing head and a bottom gear plate rotatably affixed to a bottom of said flossing head, and a space between the top gear plate and the bottom gear plate.

5. The flossing device of claim 1, further comprising a flossing adapter having a stem and said flossing head, wherein said flossing adapter is removably attached to said body.

6. The flossing device of claim 5, further comprising a light affixed to said stem.

7. The flossing device of claim 1, further comprising a light affixed to said body.

8. The flossing device of claim 1, wherein said driving mechanism is configured to move the floss side to side and forward and back with respect to said arms.

9. The flossing device of claim 1, wherein said driving mechanism is configured to move the floss side to side and forward and back with respect to said body.

10. The flossing device of claim 1, wherein said driving mechanism is configured to move the floss up and down and forward and back with respect to a gap between a user's teeth.

11. The flossing device of claim 1, wherein said floss retention device maintains the floss taut.

12. The flossing device of claim 1, wherein said two stationary arms extend forward from said body.

13. A flossing device for use with floss, said device comprising:
    a flossing head having a first stationary arm having a first distal end portion and a second stationary arm having a second distal end separate from the first distal end portion;
    a first gear housed at the first distal end portion, the first gear having a first channel;
    a second gear housed at the second distal end portion, the second gear having a second channel; and
    a flossing insert having a first pin, a second pin, floss having a first end fixedly attached to the first pin and a second end opposite the first end, the second pin fixedly attached to the second pin, wherein the first pin is removably received in the first channel and the second pin is removably received in the second channel.

14. The flossing device of claim 13, wherein the first and second gears rotate in unison so that the floss moves back and forth and up and down with respect to the first and second distal ends.

* * * * *